(12) United States Patent
Aoyama et al.

(10) Patent No.: US 6,242,410 B1
(45) Date of Patent: Jun. 5, 2001

(54) AZEOTROPIC COMPOSITION OF HEXAFLUOROPROPYLENE DIMER AND ACETONITRILE AND SEPARATION PROCESS USING THE SAME

(75) Inventors: Hirokazu Aoyama; Akikazu Tabuchi, both of Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/160,038

(22) Filed: Sep. 25, 1998

(30) Foreign Application Priority Data

Sep. 29, 1997 (JP) .................................................. 9-263933

(51) Int. Cl.[7] .............................. B01D 3/36; C07C 17/383
(52) U.S. Cl. ......................... 510/409; 510/408; 510/412; 252/67
(58) Field of Search .................................. 510/408, 409, 510/412; 252/67

(56) References Cited

U.S. PATENT DOCUMENTS 4,042,638 * 8/1977 Ozawa et al. ................. 260/653.1 R
5,387,728 * 2/1995 Gisser et al. ........................ 570/153
5,395,540 * 3/1995 Gisser et al. ............................ 252/67

FOREIGN PATENT DOCUMENTS

1511083 * 5/1978 (GB).
49-134614 12/1974 (JP).
51-125307 11/1976 (JP).

* cited by examiner

Primary Examiner—Yogendra Gupta
Assistant Examiner—Brian P. Mruk
(74) Attorney, Agent, or Firm—Birch, Stewart, Kolasch & Birch, LLP (57) ABSTRACT

There is provided an azeotropic mixture consisting substantially of a hexafluoropropylene dimer and acetonitrile.

In addition, there is provided a process for the separation of a hexafluoropropylene dimer which does not substantially contain acetonitrile, or acetonitrile which does not substantially contain a hexafluoropropylene dimer from a mixture which contains acetonitrile and the hexafluoropropylene dimer, comprising the steps of subjecting the mixture to a distillation operation and distilling off the azeotropic mixture which consists substantially of the hexafluoropropylene dimer and acetonitrile.

7 Claims, 7 Drawing Sheets

AZEOTROPIC COMPOSITION OF HEXAFLUOROPROPYLENE DIMER AND ACETONITRILE AND SEPARATION PROCESS USING THE SAME

BACKGROUND OF THE INVENTION

1. Field of the Invention

The present invention relates to an azeotropic composition (or an azeotropic mixture) of hexafluoropropylene dimer and acetonitrile and a separation processes by distillation utilizing the azeotropic composition. For example, the hexafluoropropylene dimer can be used as a heating medium for a high temperature, or a solvent, and also as a starting material for producing, for example various industrial surfactants such as a water/oil-repellent.

2. Description of the Related Art

A production process of the hexafluoropropylene dimer has been known.

The processes for selectively obtaining hexafluoropropylene dimer are disclosed in Japanese Patent Kokai Publication Nos. 49-134614 (A) and 51-125307 (A), in which, there is provided, as an example, a reaction process for the selective production of hexafluoropropylene dimer in which acetonitrile is used as a medium (or solvent). Mutual solubility of the hexafluoropropylene dimer and acetonitrile is limited, and thus, in the reaction wherein acetonitrile is used as the medium, liquid-liquid separation (namely phase separation into two liquid phases) occurs: one liquid phase is an acetonitrile phase containing a small amount of hexafluoropropylene dimer; and the other liquid phase is a hexafluoropropylene dimer phase containing a small amount of acetonitrile. There is an advantage of such a reaction in that the formed hexafluoropropylene dimer is not converted to a hexafluoropropylene trimer because a large amount of the formed hexafluoropropylene dimer is separated from the acetonitrile phase, i.e. transferred outside of the reaction system.

It is noted that in the reaction, two kinds of the following hexafluoropropylene dimers are synthesized:

(1) $(CF_3)_2CFCF=CFCF_3$ (of which normal boiling point is 48° C.); and (2) $(CF_3)_2C=CFCF_2CF_3$ (of which normal boiling point is 51° C.).

Hereinafter, the compound of formula (1) is also referred as "hexafluoropropylene dimer (1)" or simply "dimer (1)", and the compound of formula (2) is also referred as "hexafluoropropylene dimer (2)" or simply "dimer (2)." Further, hereinafter the above two compounds are also generically referred as "hexafluoropropylene dimer" or simply "dimer."

The hexafluoropropylene dimer phase obtained by the liquid-liquid separation in the above reaction does not provide the dimer of which purity is high because it contains a small amount of acetonitrile. Japanese Patent Kokai Publication No. 49-134614 (A) discloses a process for production of the dimer, comprising the step of adding water to a reaction mixture containing the dimer and acetonitrile as main components, which is followed by the liquid-liquid separation and distillation. However, the process is disadvantageous to the industrial process since acetonitrile as the solvent contains water which must be removed for reuse thereof.

SUMMARY OF THE INVENTION

The inventors have conducted studies on a separation process of acetonitrile from a hexafluoropropylene dimer phase containing acetonitrile, and found that a hexafluoropropylene dimer and acetonitrile form a minimum boiling point azeotropic composition. Further, the inventors have found a separation process in which acetonitrile or hexafluoropropylene dimer is effectively separated from a mixture comprising acetonitrile and the hexafluoropropylene dimer by utilizing the azeotropic composition with a minimum amount of loss, and thus the inventions have been completed.

In the first aspect, the present invention provides an azeotropic composition (or a mixture) which consists essentially of a hexafluoropropylene dimer and acetonitrile. Namely, the present invention provides two kinds of the azeotropic compositions: one is composed of hexafluoropropylene dimer (1) and acetonitrile; and the other is composed of hexafluoropropylene dimer (2) and acetonitrile. The azeotropic composition is useful as a reflux when a distillation is performed in order to separate one of the hexafluoropropylene dimer and acetonitrile from a mixture comprising, or preferably consisting substantially of them (e.g. a reaction product containing the synthesized hexafluoropropylene dimer).

In the second aspect, the present invention provides a process of separating acetonitrile or a hexafluoropropylene dimer from a mixture comprising the dimer and acetonitrile by subjecting the mixture to a distillation operation and distilling off an azeotropic composition which consists substantially of the dimer and acetonitrile. According to the process, acetonitrile which does not substantially contain the dimer, or the hexafluoropropylene dimer which does not substantially contain acetonitrile is available as a bottom product. For example, a concentration of the dimer or acetonitrile as an impurity of the bottom product is less than 0.1 mol %, and preferably less than 0.001 mol %.

The hexafluoropropylene dimer separated in this process may be hexafluoropropylene dimer (1) or hexafluoropropylene dimer (2) or a mixture of dimer (1) and dimer (2).

In the above separation process, substantially all of one component of the mixture is removed as the azeotropic composition by subjecting the mixture to the distillation operation, and thus, the bottom product is obtained which consists substantially of the other component. The component which is obtained as the bottom product is determined by comparing an amount of acetonitrile with an amount of the dimer in the mixture to be subjected to the distillation operation.

When the amount of acetonitrile in the mixture is larger than an amount of acetonitrile which forms, under conditions of the distillation operation, especially an operation pressure and temperature, the azeotropic composition with all the dimer in the mixture, acetonitrile can be obtained as the bottom product while the dimer is distilled off as the azeotropic composition. In other words, in case in which a ratio of acetonitrile to the dimer in the mixture is larger than a ratio of acetonitrile to the dimer in the azeotropic composition, acetonitrile which does not substantially contain the dimer can be effectively obtained as the bottom product.

To the contrary, when the ratio of acetonitrile to the dimer of the mixture is smaller than the ratio of acetonitrile to the dimer of the azeotropic composition under the conditions of the distillation operation, acetonitrile is distilled off as the azeotropic composition, while the dimer which does not substantially contain acetonitrile can be obtained as the bottom product.

When both dimers (1) and (2) are contained in the mixture, it is considered that the mixture is consisted of a mixture of dimer (1) and acetonitrile and a mixture of dimer (2) and acetonitrile. The obtainable component as the bottom product is determined by comparing the amount of acetonitrile actually contained in the mixture with a sum of the amounts of acetonitrile required to form the azeotropic compositions with all dimers (1) and (2) in the mixture under the given operation condition (especially an operation temperature and pressure).

That is, when the amount of acetonitrile in the mixture is smaller than the above sum, a mixture of dimers (1) and (2) is obtained as the bottom product. In other words, the component of which the amount is larger than the amount required to form the azeotropic compositions, is obtainable as the bottom product.

BRIEF DESCRIPTION OF THE DRAWINGS

In FIG. 7, the reference number 11 denotes a reaction vessel, 12 does a hexafluoropropylene stream, 13 does a container for dimer storage, 14 does a distillation apparatus, 15 does a container for initial distillate (azeotropic composition), and 16 does a container for main distillate (hexafluoropropylene dimer).

DETAILED DESCRIPTION OF THE INVENTION

As described above, there is provided two azeotropic compositions which have been found by the inventors for the first time.

One of them is an azeotropic composition consisting substantially of hexafluoropropylene dimer (1) and acetonitrile. A molar ratio of dimer (1) to acetonitrile (i.e. dimer (1)/acetonitrile molar ratio) is in the range of 78/22 to 85/15. An azeotropic point depends on the pressure and is in the range of 40° C. to 150° C. at a pressure (gauge pressure) in the range of 0 kg/cm$^2$-G to 20 kg/cm$^2$-G.

The other is an azeotropic composition consisting substantially of hexafluoropropylene dimer (2) and acetonitrile. A molar ratio of dimer (2) to acetonitrile (i.e. dimer (2)/acetonitrile molar ratio) is in the range of 74/26 to 81/19. An azeotropic point depends on the pressure and is in the range of 44° C. to 155° C. at a pressure (gauge pressure) in the range of 0 kg/cm$^2$-G to 20 kg/cm$^2$-G.

At a temperature adopted in a conventional industrial processes, each of these azeotropic compositions are separated in two liquid phases. For example, at a temperature in the range of about −15° C. to about 45° C., each of these azeotropic compositions separates into two liquid phases: one being a hexafluoropropylene dimer phase in which a concentration of the hexafluoropropylene dimer is relatively high, for example, about 90.0 mol % to about 98.5 mol %; and the other being an acetonitrile phase in which a concentration of acetonitrile is relatively high, for example, about 99.0 mol % to 99.9 mol %. At a temperature adopted in the most conventional industrial process, for example, from 20° C. to 40° C., the concentration of hexafluoropropylene dimer in the hexafluoropropylene dimer phase is in the range of about 91 mol % to about 96 mol %, and the concentration of acetonitrile in the acetonitrile phase is in the range of about 99.1 mol % to about 99.4 mol %.

As described above, since it has been found that acetonitrile and each of hexafluoropropylene dimers (1) and (2) form the azeotropic composition, there is provided a process of separating acetonitrile or the hexafluoropropylene dimer from a starting mixture comprising acetonitrile and a hexafluoropropylene dimer. According to the process, the dimer which does not substantially contain acetonitrile, or acetonitrile which does not substantially contain the dimer can be effectively obtained as a bottom product by subjecting the starting mixture to a distillation operation and distilling off the azeotropic composition of the dimer and acetonitrile.

In the first embodiment of the process, the starting mixture is an acetonitrile phase in which hexafluoropropylene dimer (1) is dissolved (for example saturated), and acetonitrile which does not substantially contain dimer (1) is obtained as a bottom product while an azeotropic composition which consists substantially of hexafluoropropylene dimer (1) and acetonitrile is distilled off as a distillate by the distillation operation.

In the second embodiment of the process, the starting mixture is an acetonitrile phase in which hexafluoropropylene dimer (2) is dissolved, and acetonitrile which does not substantially contain dimer (2) is obtained as a bottom product while an azeotropic composition which consists substantially of hexafluoropropylene dimer (2) and acetonitrile is distilled off as a distillate by the distillation operation.

In the third embodiment of the process, the starting mixture is a hexafluoropropylene dimer (1) phase in which acetonitrile is dissolved, and dimer (1) which does not substantially contain acetonitrile is obtained as a bottom product while an azeotropic composition which consists substantially of hexafluoropropylene dimer (1) and acetonitrile is distilled off as a distillate by the distillation operation.

In the fourth embodiment of the process, the starting mixture is a hexafluoropropylene dimer (2) phase in which acetonitrile is dissolved, and dimer (2) which does not substantially contain acetonitrile is obtained as a bottom product while an azeotropic composition which consists substantially of hexafluoropropylene dimer (2) and acetonitrile is distilled off as a distillate by the distillation operation.

When both dimers (1) and (2) are contained in the starting mixture, acetonitrile which does not substantially contain dimers (1) and (2), or a mixture of dimers (1) and (2) which does not substantially contain acetonitrile can be obtained in accordance with the process of the invention in which the starting mixture is subjected to the distillation operation and the azeotropic composition of acetonitrile and dimers (1) and (2) is distilled off.

Therefore, in the fifth embodiment of the process, the starting mixture is an acetonitrile phase in which hexafluoropropylene dimers (1) and (2) are dissolved, and acetonitrile which does not substantially contain dimer (1) or (2) is obtained as a bottom product while an azeotropic composition which consists substantially of hexafluoropropylene dimers (1) and (2) and acetonitrile is distilled off as a distillate by the distillation operation.

In the sixth embodiment of the process, the starting mixture is a hexafluoropropylene dimers (1) and (2) phase in which acetonitrile is dissolved, and the mixture of dimers (1) and (2) which does not substantially contain acetonitrile is obtained as a bottom product while an azeotropic composition which consists substantially of hexafluoropropylene dimers (1) and (2) and acetonitrile is distilled off as a distillate by the distillation operation.

In case in which the starting mixture further contains other additional component(s), for example a hexafluoropropylene trimer, in addition to the hexafluoropropylene dimer and acetonitrile, the component behaves with the azeotropic composition to be distilled off, or with the dimer or acetonitrile to be obtained as the bottom product, depending on an affinity of the component for acetonitrile and dimer and conditions of the distillation operation. There may be some cases where the component behaves with both the distillate and the bottom product.

The separation process of the present invention can be performed by a batch azeotropic distillation or a continuous azeotropic distillation using a conventional distillation apparatus. The distillation apparatus may be a packed column or a plate column each used for a general distillation operation. Operation condition of the distillation are appropriately selected by the skilled person in this art depending on the distillation apparatus, the azeotropic point, and utility limitations. In the azeotropic distillation operation, the distilled azeotropic composition is preferably used as a reflux after condensation.

The operation pressure may be, for example, in the range of 0 kg/cm$^2$-G to 20 kg/cm$^2$-G. In such a pressure range, the column top temperature is in the range of 40° C. to 150° C. The operation pressure may be preferably in the range of 0 kg/cm$^2$-G to 1 kg/cm$^2$-G. In such a pressure range, the column top temperature is in the range of 40° C. to 64° C. The number of plates of the plate column or a packing height of the packed column can be appropriately selected depending on the composition of the starting mixture fed thereto, a reflux ratio, and degrees of separation of the distillate and the bottom product, for example, an impurity concentration.

The separation process of the present invention can be preferably applied to the dimerizing reaction of hexafluoropropylene in which hexafluoropropylene is continuously charged into a reaction vessel such as an autoclave. In the reaction, acetonitrile as a reaction solvent and KF as a catalyst are used. In that case, a hexafluoropropylene dimer phase in which acetonitrile is dissolved can be obtained by the liquid-liquid separation after the reaction. By subjecting the dimer phase to a distillation operation, acetonitrile in the phase can be distilled off with hexafluoropropylene dimer as the azeotropic composition, and thus the residual dimer can be obtained as a bottom product.

Therefore, the present invention provides a process for the production of a hexafluoropropylene dimer in which acetonitrile is used as a reaction medium (or solvent). The process comprises the following steps of:

(a) producing a reaction product comprising acetonitrile and a hexafluoropropylene dimer;

(b) separating the reaction product into two liquid phases so as to obtain a hexafluoropropylene dimer phase comprising acetonitrile;

(c) subjecting the hexafluoropropylene dimer phase to a distillation operation;

(d) distilling off an azeotropic composition consisting substantially of acetonitrile and the hexafluoropropylene dimer; and (e) withdrawing a bottom product comprising the hexafluoropropylene dimer which dose not substantially contain acetonitrile.

The present invention also provides a recovery process of acetonitrile in the production process of a hexafluoropropylene dimer in which acetonitrile is used as reaction medium, which recovery process comprises the steps of:

(a) producing a reaction product comprising acetonitrile and a hexafluoropropylene dimer;

(b') separating the reaction product into two liquid phases so as to obtain an acetonitrile phase comprising the dimeried hexafluoropropylene;

(c') subjecting the acetonitrile phase to a distillation operation;

(d) distilling off the azeotropic composition consisting substantially of acetonitrile and the hexafluoropropylene dimer; and (e') withdrawing a bottom product comprising acetonitrile which dose not substantially contain the hexafluoropropylene dimer.

This recovery process is preferably incorporated in the above production process of the hexafluoropropylene dimer.

The production process of the hexafluoropropylene dimer according to the present invention can be performed as follows:

As mentioned in the above, the reaction process of synthesizing the hexafluoropropylene dimer from hexafluoropropylene in which acetonitrile is used as the reaction catalyst has been known. As to the process, reference may be made to Japanese Patent Kokai Publications Nos. 49-134614 (A) and 51-125307 (A) and the contents of these publications are incorporated herein by the reference.

A hexafluoropropylene dimer phase containing acetonitrile, which is produced by the above reaction process, is charged into a distillation column, preferably a rectification column, and then distilled at atmospheric pressure or under pressure. In case in which the distillation is performed in a batch mode, an azeotropic composition of acetonitrile and the hexafluoropropylene dimer is distilled off as an initial distillate, and then hexafluoropropylene dimer which does not substantially contain acetonitrile is obtained as a bottom product. Alternatively, the hexafluoropropylene dimer is also distilled off and collected after an initial distillate is distilled off. The latter case provides an advantage in that the hexafluoropropylene dimer does not contain other higher boiling component(s).

The azeotropic composition as the initial distillate separates into an acetonitrile phase containing the hexafluoropropylene dimer and a hexafluoropropylene dimer phase containing acetonitrile when it is condensed. The former phase can be recycled for the reaction while the latter phase can be recycled to a distillation apparatus. Therefore, the liquid-liquid separation operation may be performed for such recycling. Alternatively, all the initial distillate can be recycled to the reaction vessel. In any way, the hexafluoropropylene dimer can be separated with a minimum loss.

The above distillation operation can be carried out also continuously. In that case, the hexafluoropropylene dimer phase containing acetonitrile is fed to a first distillation column (azeotropic distillation column), and then the azeotropic composition consisting substantially of the hexafluoropropylene dimer and acetonitrile is distilled off so that the hexafluoropropylene dimer which dose not substantially contain acetonitrile is obtained as the bottom product. The obtained bottom product may be fed into a second distillation column (rectification column) in order to distill the hexafluoropropylene dimer, whereby a high-purity hexafluoropropylene dimer which does not contain one or more components having a higher boiling point.

In the above reaction to produce the dimer, the liquid-liquid separation operation after the reaction provides the acetonitrile phase containing the dimer dissolved, which phase can be reused as the medium for the dimerizing reaction as it is. Therefore, usually it is not necessary to purify the phase to obtain pure acetonitrile. However, if it is desired to separate acetonitrile, acetonitrile can be separated from the phase in accordance with the procedures described in the following.

The acetonitrile phase containing the hexafluoropropylene dimer is charged into a distillation column, and the distillation is carried out at atmospheric pressure or under pressure. The azeotropic composition consisting substantially of the hexafluoropropylene dimer and acetonitrile is distilled off as an initial distillate, and then acetonitrile which dose not substantially contain hexafluoropropylene dimer is obtained as a bottom product, or as a distillate by further distilling off.

In the same way as in above described treatment of the dimmer phase, the initial distillate i.e. the azeotropic composition may be separated again into the acetonitrile phase containing dimer and the hexafluoropropylene dimer phase containing acetonitrile. Then, the acetonitrile phase can be returned to the dimerizing reaction process or to the distillation column. On the other hand, the hexafluoropropylene dimer phase can be fed to the distillation column in which the hexafluoropropylene dimer phase obtained from the reaction product is distilled. In this way, acetonitrile can be separated with a minimum loss. This distillation can be carried out in a continuous operation or in a batch operation.

The present inventions will be, hereinafter, explained in further detail with reference to Examples.

EXAMPLE 1

The mutual solubility (liquid-liquid equilibrium) of the hexafluoropropylene dimer and acetonitrile was measured in the following manner.

Figure 1:
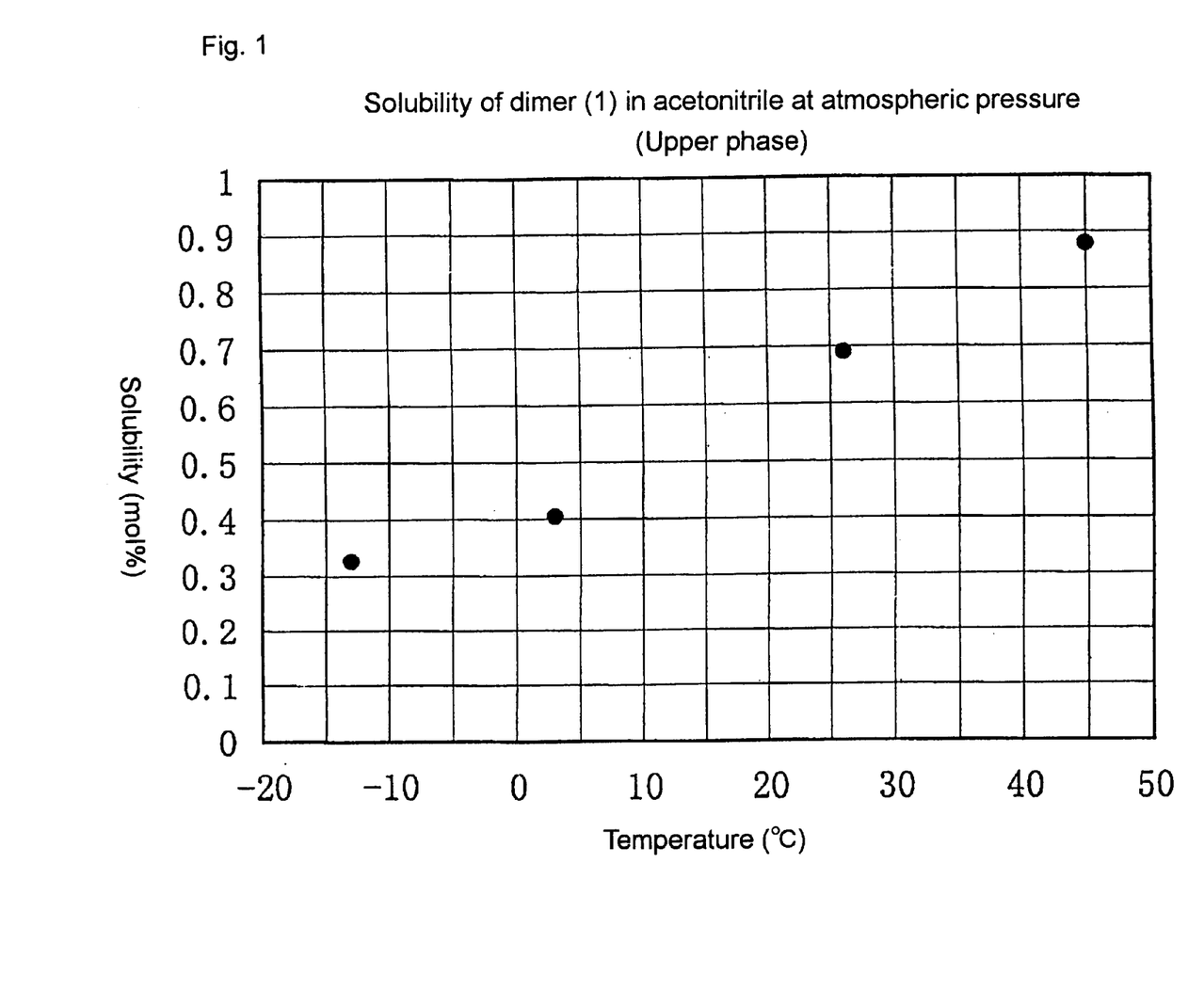
FIG. 1 is a graph showing results of measurement of solubility of hexafluoropropylene dimer (1) in acetonitrile in an upper liquid phase.
Figure 2:
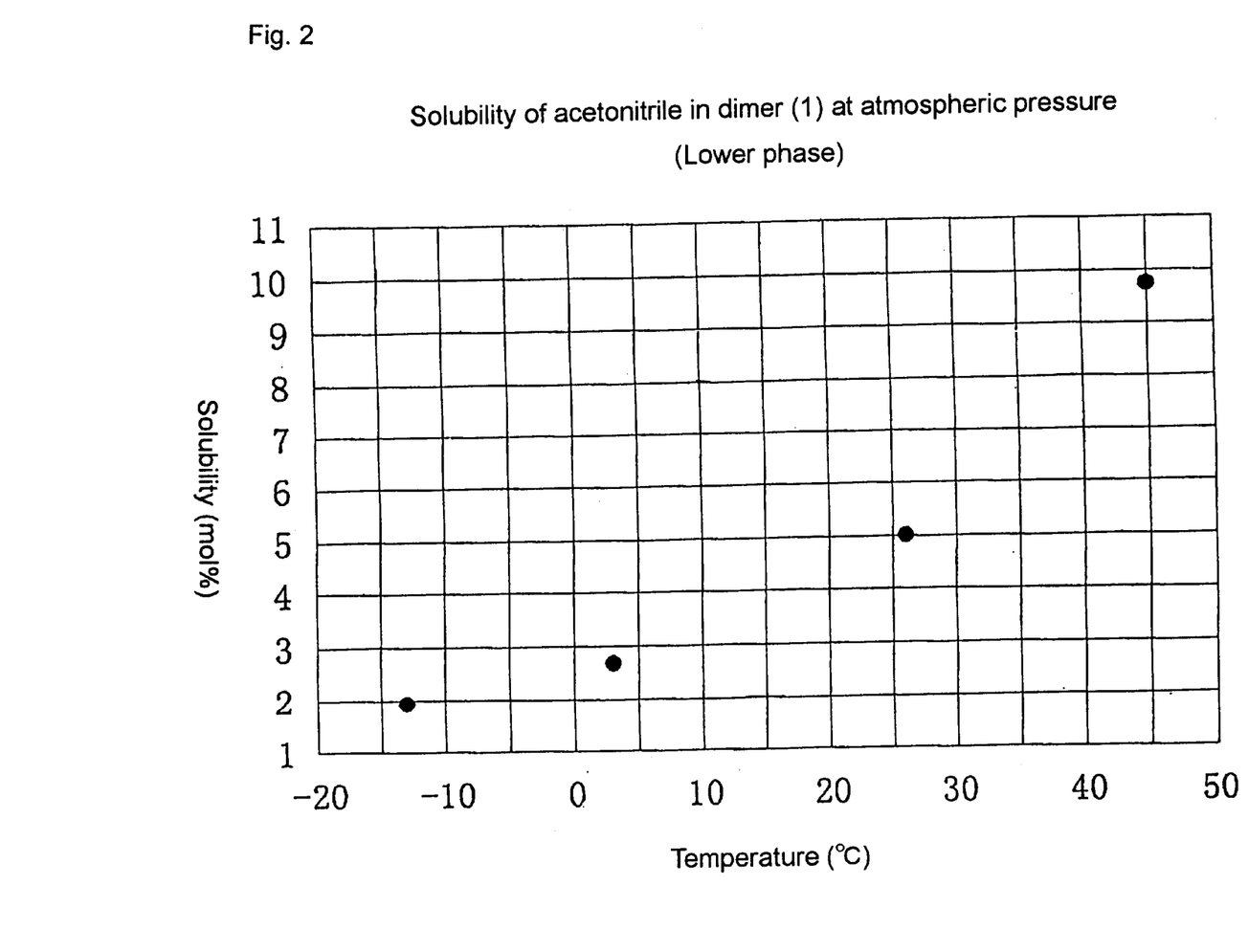
FIG. 2 is a graph showing results of measurement of solubility of acetonitrile in hexafluoropropylene dimer (1) in a lower liquid phase.

15 Grams of acetonitrile and 15 g of hexafluoropropylene dimer (1) or (2) were charged into a vial having septum cap (effective volume 30 ml) and stirred for 24 hours at a predetermined temperature. After stirring, the vial was left for 12 hours at that temperature in order to separate the mixture into the upper liquid phase and the lower liquid phase. The composition of each phase was determined by means of gas chromatography. The results are shown in Tables 1 and 2 below, and also the results of Table 1 are shown in FIGS. 1 and 2.

TABLE 1

Mutual solubility of hexafluoropropylene dimer (1)/acetonitrile

| Temperature | Lower phase (mol %) | | Upper phase (mol %) | |
| --- | --- | --- | --- | --- |
| (° C.) | Acetonitrile | Dimer (1) | Acetonitrile | Dimer (1) |
| −13 | 1.93 | 98.07 | 99.67 | 0.33 |
| 3 | 2.69 | 97.31 | 99.59 | 0.41 |
| 26 | 5.00 | 95.00 | 99.31 | 0.69 |
| 45 | 9.76 | 90.24 | 99.12 | 0.88 |

TABLE 2

Mutual solubility of hexafluoropropylene dimer (2)/acetonitrile

| Temperature | Lower phase (mol %) | | Upper phase (mol %) | |
| --- | --- | --- | --- | --- |
| (° C.) | Acetonitrile | Dimer (2) | Acetonitrile | Dimer (2) |
| −13 | 5.09 | 94.91 | 99.84 | 0.16 |
| 3 | 5.48 | 94.52 | 99.78 | 0.22 |
| 26 | 6.15 | 93.85 | 99.66 | 0.34 |
| 45 | 6.75 | 93.25 | 99.53 | 0.47 |

These results show that the hexafluoropropylene dimer and acetonitrile do not solve with each other infinitely but the mutual solubility of them has a limit over a wide temperature range, i.e. the temperature range which is practically adopted in an industrial process.

EXAMPLE 2

The vapor-liquid equilibrium of the hexafluoropropylene dimer and acetonitrile system was measured in the following manner.

A mixture of the hexafluoropropylene dimer and acetonitrile having such a composition that they are dissolved with each other was charged into a round flask (effective volume 200 ml) equipped with a Dimroth condenser. Then a still portion thereof was heated in a mantle heater. After the system reached its equilibrium state, samples were obtained from the vapor phase and the liquid phase, and compositions of them were analyzed.

A mixture of the hexafluoropropylene dimer and acetonitrile having such a composition that they are not dissolved with each other (i.e. a mixture separable into two liquid phases) was charged into a round flask (effective volume 1 little) equipped with a Dimroth condenser. Then the still portion thereof was heated in a mantle heater. After the system reached its equlibrium state, a sample (about 1 ml) was obtained from the vapor phase, which was dissolved in a freon medium, and then the composition of the sample was analyzed by means of gas chromatography.

In this example, the compositions of the liquid phase were regarded as the same as the composition of the mixture which was initially charged into the still because the liquid phase was excessively large in its amount over the vapor phase.

Figure 3:
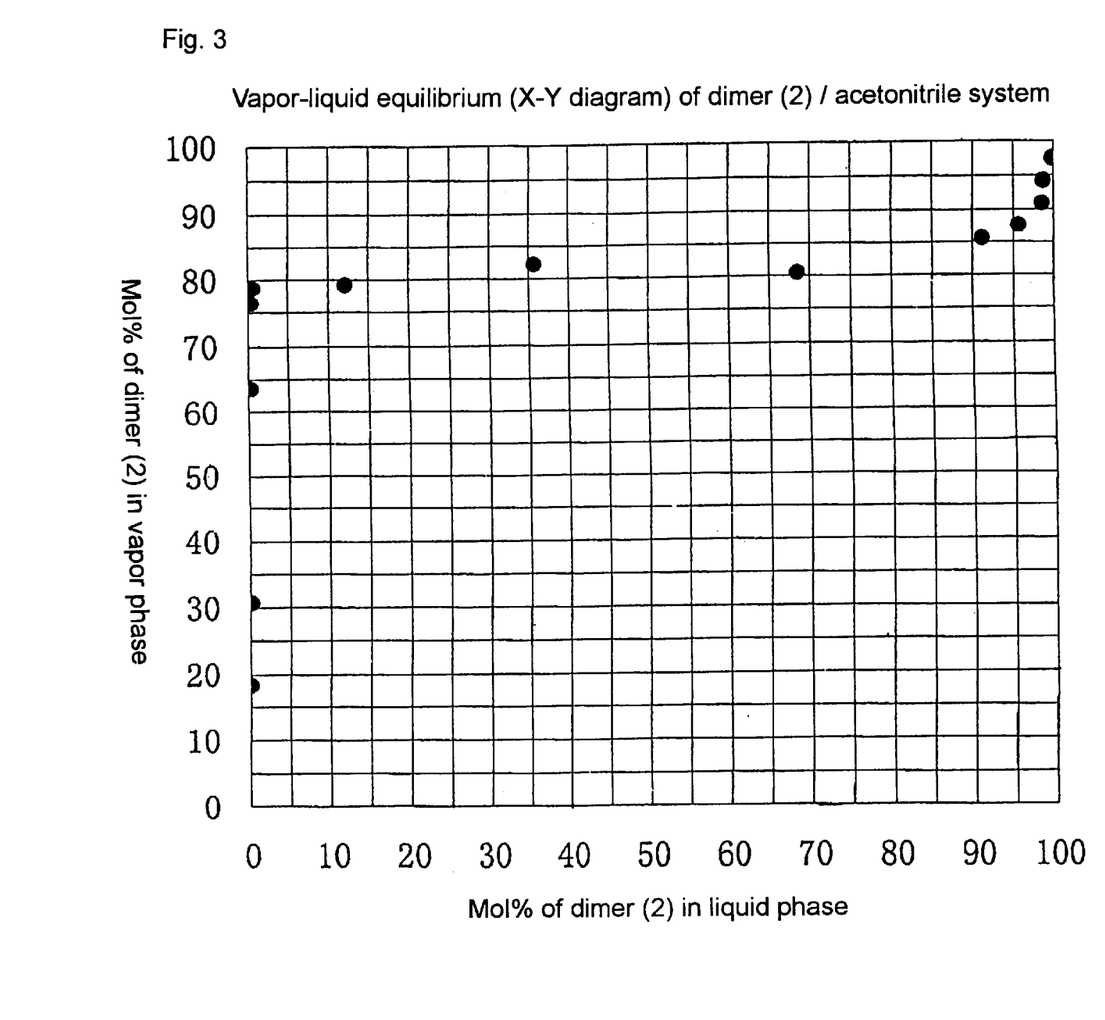
FIG. 3 is a graph showing a vapor-liquid equilibrium relationship of acetonitrile/hexafluoropropylene dimer (2) system at atmospheric pressure.
Figure 4:
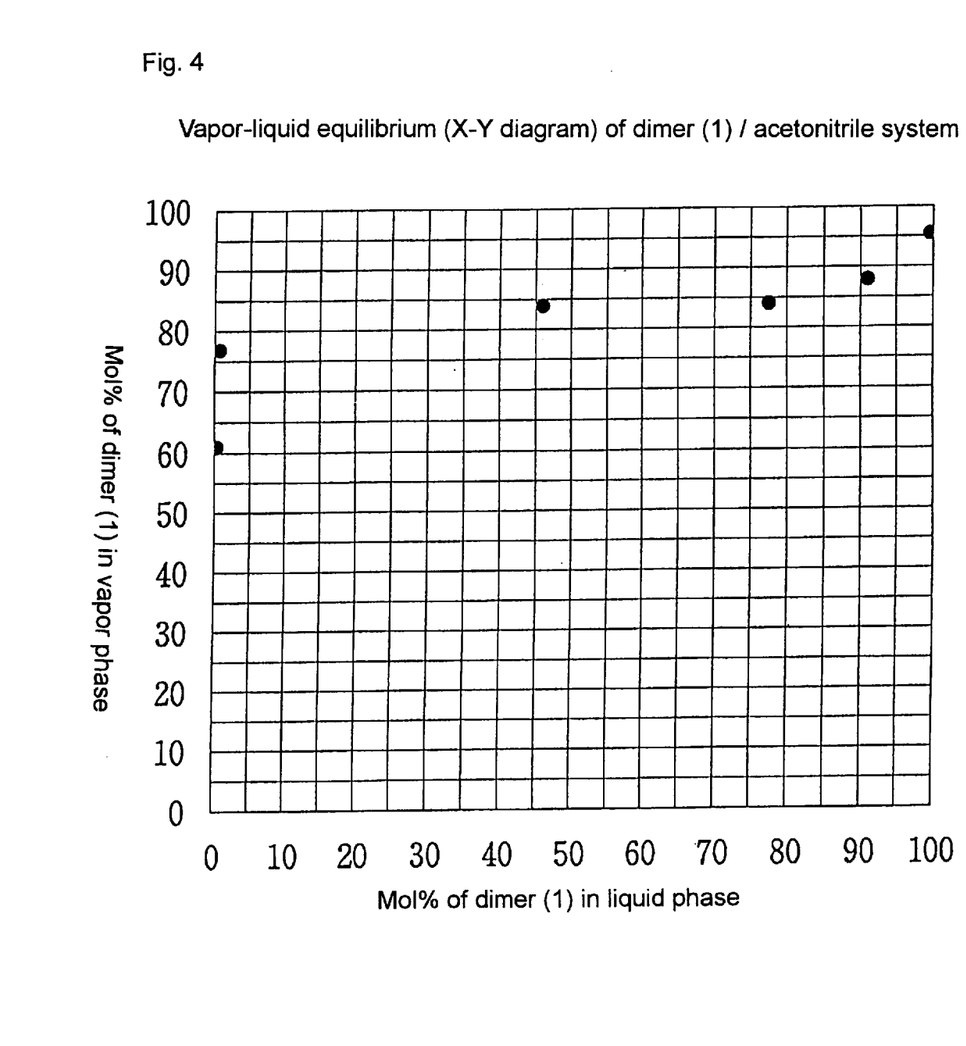
FIG. 4 is a graph showing a vapor-liquid equilibrium relationship of acetonitrile/hexafluoropropylene dimer (1) system at atmospheric pressure.

The results are shown in Tables 3 and 4. The results are also shown in FIGS. 3 and 4.

TABLE 3

Vapor-liquid equilibrium of hexafluoropropylene dimer (2)/acetonitrile system

| Still Temp. | Composition of liquid phase (mol %) | | Composition of vapor phase (mol %) | |
| --- | --- | --- | --- | --- |
| (° C.) | Acetonitrile | Dimer (2) | Acetonitrile | Dimer (2) |
| 50.0 | 0.194 | 99.806 | 2.416 | 97.584 |
| 49.0 | 1.301 | 98.699 | 5.741 | 94.259 |
| 49.0 | 1.416 | 98.584 | 9.093 | 90.907 |
| 46.0 | 4.315 | 95.685 | 12.457 | 87.543 |
| 46.0 | 87.925 | 12.075 | 20.766 | 79.234 |
| 46.0 | 64.380 | 35.620 | 17.800 | 82.200 |

TABLE 3-continued

Vapor-liquid equilibrium of hexafluoropropylene dimer (2)/acetonitrile system

| Still Temp. | Composition of liquid phase (mol %) | | Composition of vapor phase (mol %) | |
|---|---|---|---|---|
| (° C.) | Acetonitrile | Dimer (2) | Acetonitrile | Dimer (2) |
| 46.0 | 8.832 | 91.168 | 14.359 | 85.641 |
| 46.0 | 31.517 | 68.483 | 19.408 | 80.592 |
| 78.0 | 99.939 | 0.061 | 81.727 | 18.273 |
| 73.0 | 99.829 | 0.171 | 69.280 | 30.720 |
| 68.0 | 99.731 | 0.269 | 36.423 | 63.577 |
| 64.0 | 99.565 | 0.435 | 23.570 | 76.430 |
| 57.0 | 99.406 | 0.594 | 21.291 | 78.709 |

TABLE 4

Vapor-liquid equilibrium of hexafluoropropylene dimer (1)/acetonitrile system

| Still Temp. | Composition of liquid phase (mol %) | | Composition of vapor phase (mol %) | |
|---|---|---|---|---|
| (° C.) | Acetonitrile | Dimer (1) | Acetonitrile | Dimer (1) |
| 45.0 | 0.466 | 99.534 | 4.519 | 95.481 |
| 41.0 | 9.000 | 91.000 | 12.057 | 87.943 |
| 40.0 | 22.505 | 77.495 | 15.940 | 84.060 |
| 40.0 | 53.981 | 46.019 | 16.112 | 83.888 |
| 68.0 | 99.272 | 0.728 | 23.184 | 76.816 |
| 70.0 | 99.699 | 0.301 | 38.995 | 61.005 |

The obtained X-Y diagrams apparently show that each of hexafluoropropylene dimers (1) and (2) forms the azeotropic composition with acetonitrile. The azeotropic molar ratio of dimer (1)/acetonitrile is in the range of 80/20 to 83/17 at atmospheric pressure, and the azeotropic molar ratio of dimer (2)/acetonitrile is in the range of 84/16 to 87/13 at atmospheric pressure.

EXAMPLE 3

Figure 5:
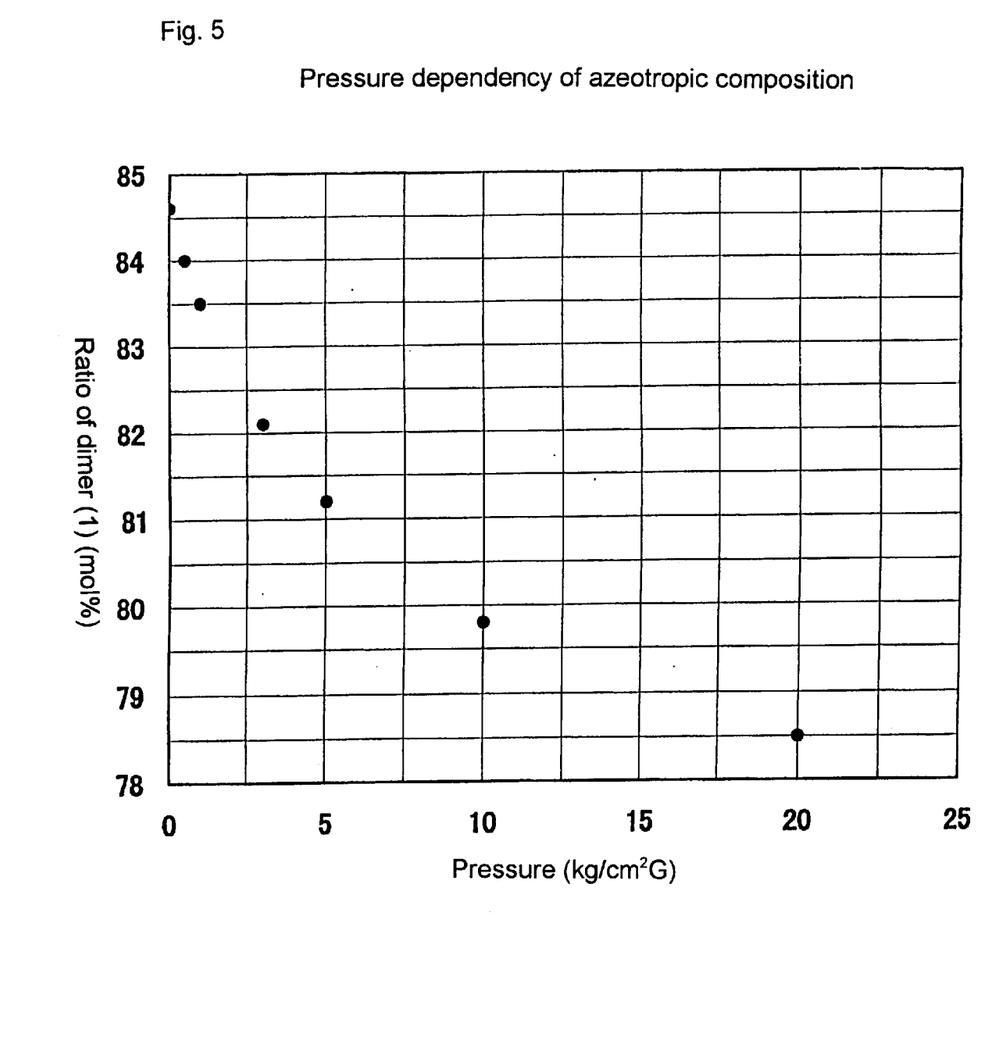
FIG. 5 is a graph showing pressure dependency of azeotropic composition (ratio of dimer (1) (mol %)).
Figure 6:
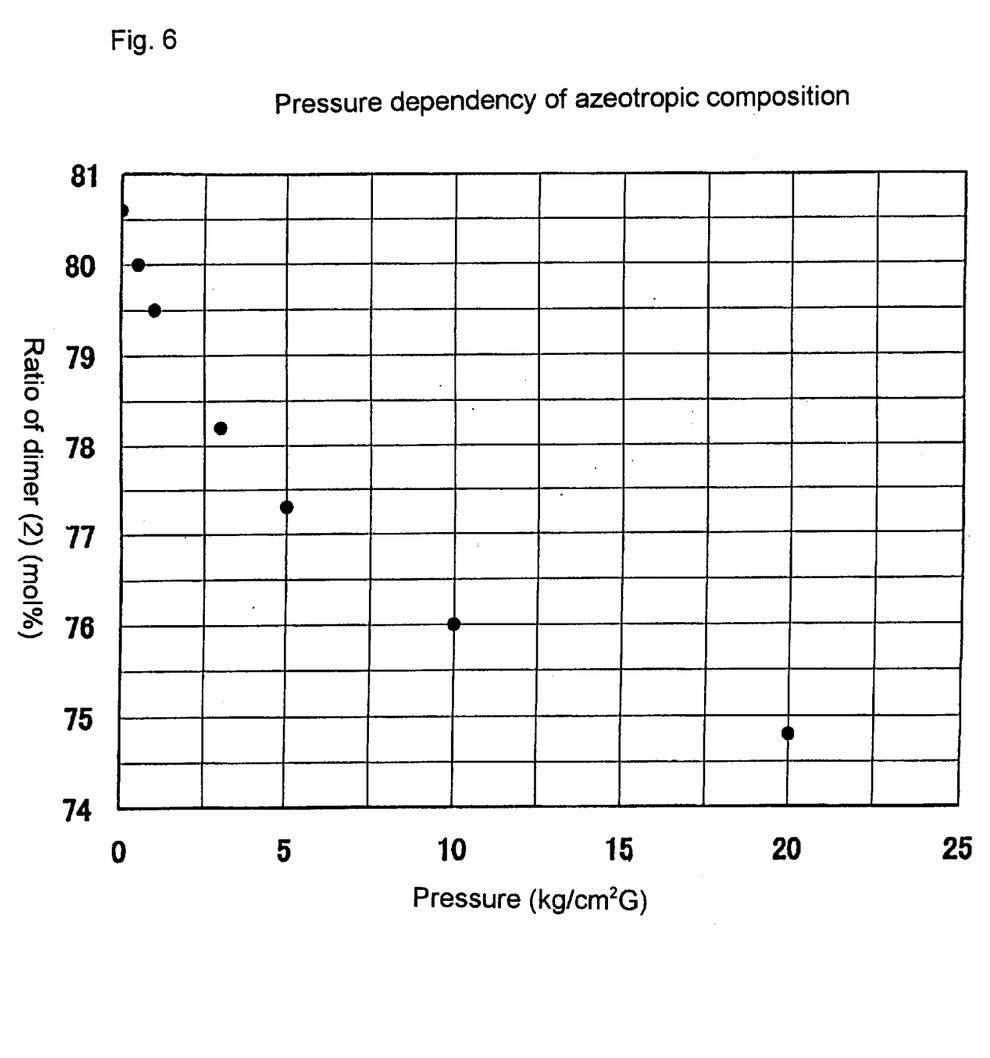
FIG. 6 is a graph showing pressure dependency of azeotropic composition (ratio of dimer (2) (mol %)).

The vapor-liquid equilibrium was measured as in Example 2 at various system pressures. The azeotropic point (or azeotropic temperature) and the molar ratio of dimer in the azeotropic composition were measured at each pressure. The results are shown in Tables 5 and 6. The results are also shown in FIGS. 5 and 6.

TABLE 5

Azeotropic point and the molar ratio of dimer (1) in azeotropic composition

| Pressure ($kg/cm^2$-G) | Temperature (° C.) | Ratio of dimer (1) (mol %) |
|---|---|---|
| 0 | 40.0 | 84.6 |
| 0.5 | 50.8 | 84.0 |
| 1 | 59.0 | 83.5 |
| 3 | 81.1 | 82.1 |
| 5 | 95.8 | 81.2 |
| 10 | 120.3 | 79.8 |
| 20 | 149.6 | 78.5 |

TABLE 6

Azeotropic point and the molar ratio of dimer (2) in azeotropic composition

| Pressure ($kg/cm^2$-G) | Temperature (° C.) | Ratio of dimer (2) (mol %) |
|---|---|---|
| 0 | 44.0 | 80.6 |
| 0.5 | 54.9 | 80.0 |
| 1 | 63.2 | 79.5 |
| 3 | 85.7 | 78.2 |
| 5 | 100.5 | 77.3 |
| 10 | 125.3 | 76.0 |
| 20 | 155.0 | 74.8 |

EXAMPLE 4

In this example, the hexafluoropropylene dimer was produced. The production is explained with reference to FIG. 7, which schematically shows a flow sheet of the process for the production of the hexafluoropropylene dimer.

Figure 7:
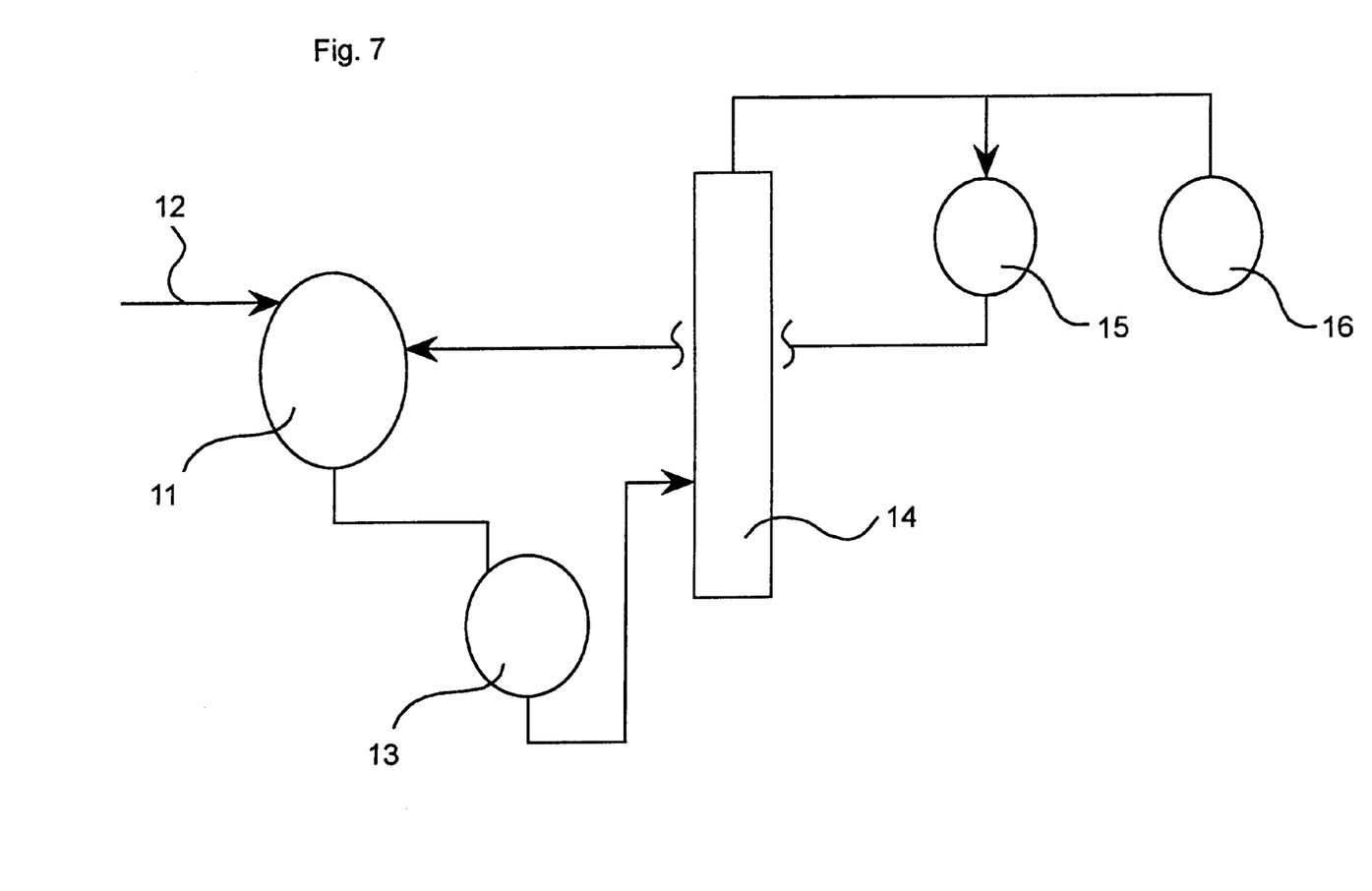
FIG. 7 schematically shows a flow sheet of one embodiment of a process for the production of a hexafluoropropylene dimer according to the present invention.

55 Grams of a medium (acetonitrile) and 2 g of a catalyst (potassium fluoride) were charged into an autoclave (a reaction vessel) (11), and then hexafluoropropylene (12) was fed to the autoclave (11) continuously at a flow rate of 35 cc/min at a reaction temperature of 25° C. The reaction was continued for 140 minutes at a reaction pressure 2.2 $kg/cm^2$-G, and then the feed of hexafluoropropylene is stopped to stop the reaction. The vessel was left and the reaction product was separated into two liquid phases.

31 Grams of the hexafluoropropylene dimer in which 9.0 mol % of acetonitrile was dissolved was obtained as the lower liquid phase while 56 g of the acetonitrile phase in which 1.1 mol % of the hexafluoropropylene dimer was dissolved was obtained as the upper liquid phase. The lower phase was withdrawn from the vessel (11) and stored in a container (13). The upper phase was left in the vessel (11), and the production operation was repeated under the same conditions by feeding fresh hexafluoropropylene to the vessel and only the lower phase was withdrawn from the vessel (11) and stored in the container (13).

The above reaction operation was repeated until 300 g of the lower phase was stored in the container. Then, the lower phase was supplied to a distillation column (14) and the distillation was performed under a top operation pressure of 0 $kg/cm^2$-G. Firstly, an azeotropic composition was obtained as an initial distillate at a top temperature of 41° C. and stored in a container (15) for the initial distillate. A total amount of the initial distillate was 60 g. In the initial distillate, the lower liquid phase was the hexafluoropropylene dimer phase in which acetonitrile was dissolved while the upper liquid phase was the acetonitrile phase in which hexafluoropropylene dimer was dissolved. In this example, the initial distillate was returned to the reaction vessel (11) for the further reaction.

Following the initial distillate, a main distillate was distilled off and stored in a container (16) for the main distillate. A total amount of the main distillate was 200 g in the container (16) while an amount of the residual in the still was 40 g. The main distillate was high-purity hexafluoropropylene dimer which did not contain substantially acetonitrile (the concentration of acetonitrile was not more than 0.001 mol %) and such purity was high enough to be used as a product for a predetermined application.

What is claimed is:

1. An azeotropic composition consisting of a hexafluoropropylene dimer and acetonitrile.

2. The azeotropic composition according to claim 1, wherein the hexafluoropropylene dimer is $(CF_3)_2CFCF=CFCF_3$ and a molar ratio of the hexafluoropropylene dimer/acetonitrile is in the range of 78/22 to 85/15.

3. The azeotropic composition according to claim 1, wherein the hexafluoropropylene dimer is $(CF_3)_2C=CFCF_2CF_3$ and a molar ratio of the hexafluoropropylene dimer/acetonitrile is in the range of 74/26 to 81/19.

4. The azeotropic composition according to claim 2, wherein under pressure in a range of 0 kg/cm$^2$-G to 20 kg/cm$^2$-G, the composition has a boiling point in a range of 40° C. to 150° C.

5. The azeotropic composition according to claim 3, wherein under pressure in a range of 0 kg/cm$^2$-G to 20 kg/cm$^2$-G, the composition has a boiling point in a range of 44° C. to 155° C.

6. A process for the separation of a hexafluoropropylene dimer or acetonitrile from a mixture which consists of the hexafluoropropylene dimer and acetonitrile, comprising the steps of subjecting the mixture to a distillation operation and distilling off an azeotropic composition which consists of the hexafluoropropylene dimer and acetonitrile.

7. The process according to claim 6, in which the hexafluoropropylene dimer is any of $(CF_3)_2CFCF=CFCF_3$, $(CF_3)_2C=CFCF_2CF_3$ and a mixture of $(CF_3)_2CFCF=CFCF_3$ and $(CF_3)_2C=CFCF_2CF_3$.

* * * * *